United States Patent
Andersen et al.

(10) Patent No.: US 7,192,768 B2
(45) Date of Patent: Mar. 20, 2007

(54) **SYNCHRONIZATION OF THE CYTOPLASMATIC AND THE NUCLEAR MATURATION OF OOCYTES *IN VITRO***

(75) Inventors: Claus Yding Andersen, Copenhagen O (DK); Anne Grete Byskov, Gentofte (DK)

(73) Assignee: Novo Nordisk A/S, Bagsvaerd (DK)

( * ) Notice: Subject to any disclaimer, the term of this patent is extended or adjusted under 35 U.S.C. 154(b) by 355 days.

(21) Appl. No.: 10/263,955

(22) Filed: Oct. 3, 2002

(65) Prior Publication Data

US 2003/0157707 A1 Aug. 21, 2003

Related U.S. Application Data

(63) Continuation of application No. PCT/DK01/00239, filed on Apr. 6, 2001.

(30) Foreign Application Priority Data

Apr. 6, 2002 (DK) ............... 2000 00585
Apr. 18, 2002 (DK) ............... 2000 00679

(51) Int. Cl.
  *C12N 5/00* (2006.01)
(52) U.S. Cl. .............. 435/325; 435/366; 435/384; 435/387; 435/404; 435/405; 435/406; 435/2
(58) Field of Classification Search ............... 435/325, 435/366, 384, 387, 404, 405, 406, 2
See application file for complete search history.

(56) References Cited

U.S. PATENT DOCUMENTS 4,987,080 A * 1/1991 Grob et al. ............ 435/379
6,518,262 B1 * 2/2003 Leysen et al. ............ 514/182

FOREIGN PATENT DOCUMENTS

CA 2199663 A1 9/1998
WO WO 99/61010 A2 12/1999
WO WO 01/38493 A1 5/2001

OTHER PUBLICATIONS

Lu, Zhongxian, et al., Molecular and Cellular Endocrinology 164 (2000) 191-196.
Tsafriri, A., et al., Molecular Human Reproduction vol. 4, No. 5, pp. 483-489, 1998.
J. Smith et al., Human Reproduction, (1999), vol. 14, pp. 145-161.

* cited by examiner

*Primary Examiner*—Leon B. Lankford, Jr.
(74) *Attorney, Agent, or Firm*—Richard W. Bork; Reza Green; Marc A. Began

(57) ABSTRACT

The present invention relates to a method for in vitro maturation of oocytes comprising the steps of:
(a) culturing one or more GV oocytes in a culture medium, the culture medium comprising a nuclear maturation inhibiting substance and comprising one or more gonadotropins and/or one or more growth factors, the culturing taking place for a time period sufficient for cytoplasmatic maturation to occur;
(b) washing the GV oocytes of step (a) to remove the nuclear maturation inhibiting substance;
(c) culturing the washed oocytes of step (b) in a culture medium comprising one or more gonadotropins and/or one or more growth factors and/or MAS for a time period sufficient for nuclear maturation.

The invention also relates to an oocyte culture medium comprising a nuclear maturation inhibiting substance and comprising one or more gonadotropins and/or one or more growth factors. The nuclear maturation inhibiting substance may be a MAS antagonist or an FF-MAS synthesis inhibitor, preferably a cytochrome P450 lanosterol 14α-demethylase (P45014DM) inhibitor e.g. ketoconazole or 22-hydroxycholesterol. The one or more gonadotropins and/or one or more growth factors are preferably a combination of EGF and FSH and/or LH.

The invention also relates to the use of a nuclear maturation inhibiting substance and one or more gonadotropins and/or one or more growth factors as described above for the preparation of a cell culture medium for in vitro maturation of oocytes.

12 Claims, No Drawings

SYNCHRONIZATION OF THE CYTOPLASMATIC AND THE NUCLEAR MATURATION OF OOCYTES IN VITRO

CROSS-REFERENCE TO RELATED APPLICATIONS

The present application claims the benefit under 35 U.S.C. 119 of Danish application nos. PA 2000 00585 filed on Apr. 6, 2000 and PA 2000 00679 filed on Apr. 18, 2002, and the continuation of PCT/DK01/00239 filed on Apr. 6, 2001, the contents of which are hereby incorporated by reference.

FIELD OF INVENTION

The present invention relates to the use of a new principle for improving the viability and pregnancy potential of oocytes and pre-embryos obtained in connection with in vitro maturation, in vitro fertilization and pre-embryo transfer treatment. More specifically, the application relates to improvement of the pregnancy potential of oocytes and pre-embryos by specifically controlled synchronization of the cytoplasmatic and nuclear maturation of the oocytes during the process in which the in vitro maturation takes place. This is done by a selective and reversible inhibition of the nuclear maturation in the presence of gonadotropins thereby allowing for a sufficient cytoplasmatic maturation of the oocytes to occur.

BACKGROUND OF THE INVENTION

Couples seeking infertility treatment will often be subject to in vitro fertilization treatment (IVF), wherein the meeting between an oocyte and a spermatozoa takes place outside the body. The woman is most commonly receiving treatment with exogenous hormones in order to regulate and stimulate the ovaries to develop more than the usual one preovulatory follicle which is seen during the natural menstrual cycle. Part of the treatment involves retrieving the oocytes from the preovulatory follicles of the ovaries in order for the oocytes to be matured and/or fertilised in vitro. After fertilisation and pre-embryo development, one to three pre-embryos are replaced in the woman's uterus, and she thus has the possibility of becoming pregnant and carry her own child. IVF is now an established treatment, which has been performed on a large scale for more than 20 years.

The protocols normally used for administration of exogenous gonadotropins are numerous and not without risks and disadvantages. The major disadvantages includes the risk of achieving ovarian hyper stimulation syndrome (OHSS) which in severe cases may be life-threatening, the economic costs to the couple, side effects from the gonadotropin preparations including weight gain, bloating, nausea, vomiting, the time involved with the monitoring process, and the unknown long-term cancer risk.

One way to alleviate the risks, side effects, and economic disadvantages of controlled ovarian stimulation protocols would be to retrieve immature oocytes and mature them in vitro. This approach would imply that the woman was without stimulation or received a minimal stimulation, whereas the retrieved oocytes in vitro could be subjected to hormonal treatment. Instead of stimulating the oocytes through the circulation of the woman, the oocytes could be stimulated directly in the culture dish. Obviously, this would primarily reduce/eliminate a number of the side effects mentioned above and secondary reduce the amounts of hormones used for the treatment.

Therefore, a number of studies have focused on the in vitro maturation (IVM) of human oocytes—and oocytes from other mammalian species. Successful maturation of human oocytes obtained from follicles which have not been affected by the mid-cycle surge of gonadotropins or a large bolus of exogenous hCG has been reported (Cha, et al, 1991, Trounson et al., 1994, Barnes et al., 1996, Russell et al., 1997, Mikkelsen, 1999).

The criteria for success were measured as the ability of the oocyte to sustain fertilization, often in connection with intracytoplasmic sperm injection (ICSI). However, the developmental competence of the embryos after replacement in the uterus is low and only a small number of babies has been born resulting from in vitro maturation of oocytes (Trounson et al., 1994, Barnes et al., 1996, Cha and Chian, 1998, Mikkelsen et al., 1999).

SUMMARY OF INVENTION

The present invention relates to a method for in vitro maturation of oocytes comprising the steps of:
(a) culturing one or more GV oocytes in a culture medium, the culture medium comprising a nuclear maturation inhibiting substance and comprising one or more gonadotropins and/or one or more growth factors, the culturing taking place for a time period sufficient for cytoplasmatic maturation to occur;
(b) washing the GV oocytes of step (a) to remove the nuclear maturation inhibiting substance;
(c) culturing the washed oocytes of step (b) in a culture medium comprising one or more gonadotropins and/or one or more growth factors and/or MAS for a time period sufficient for nuclear maturation.

The invention also relates to an oocyte culture medium comprising a nuclear maturation inhibiting substance and comprising one or more gonadotropins and/or one or more growth factors. The nuclear maturation inhibiting substance may be a MAS antagonist or an FF-MAS synthesis inhibitor, preferably a cytochrome P450 lanosterol 14α-demethylase (P45014DM) inhibitor e.g. ketoconazole or 22-hydroxycholesterol. The one or more gonadotropins and/or one or more growth factors are preferably a combination of EGF and FSH and/or LH.

The invention also relates to the use of a nuclear maturation inhibiting substance and one or more gonadotropins and/or one or more growth factors as described above for the preparation of a cell culture medium for in vitro maturation of oocytes.

DESCRIPTION OF INVENTION

Mammalian oocytes are arrested in the prophase of the first meiotic division characterized by the presence of the nuclear membrane, i.e. germinal vesicle (GV). When the oocyte resumes meiosis, it is visualized by the germinal vesicle break down (GVBD), "nuclear maturation". In the follicle, the oocytes stay in the GV stage as a result of the substances such as hypoxanthine (HX), which maintain high levels of cAMP within the oocyte, thereby preventing it from resuming meiosis. Oocytes also remain in the GV stage when cultured in the presence of physiological concentrations of HX or analogs of cAMP, such as dibutyric cyclic adenosine monophosphate, dbc-cAMP, and resume meiosis only if HX or dbc-cAMP is removed. The inhibitory effect of HX and dbc-cAMP on the nuclear maturation in cumulus enclosed oocytes as well as cumulus deprived, naked oocytes, can be overcome be adding meiosis activating sterols, e.g. FF-MAS (4,4-dimethyl-5α-cholesta-8,14,24-triene-3β-ol) or T-MAS (4,4-dimethyl-5α-cholesta-8,24-diene-3β-ol). FF-MAS was isolated and characterised from human follicular fluid and T-MAS from bull testis (Byskov et al., 1995). The sterols are intermediates in the cholesterol biosynthetic pathway from lanosterol (Schroepfer et al., 1972) (FIG.1).

The synthesis of FF-MAS from lanosterol is catalysed by cytochrome P450 lanosterol 14α-demethylase (P45014DM) encoded by the CYP51 gene. FF-MAS is converted to T-MAS by the enzyme Δ14-reductase (Δ14R). Various drugs, which are used to lower plasma cholesterol, affect the synthesis of FF-MAS and T-MAS. One drug, AY-9944-A-7 (AY), selectively inhibits the activity of Δ14R and thereby causes accumulation of FF-MAS. A recent study showed that AY added to cumulus enclosed oocytes causes accumulation of FF-MAS simultaneously with a dose-dependant induction of resumption of meiosis. Another drug, ketoconazole, can inhibit steroidogenesis at several points, including an effect on P45014DM.

Cytoplasmatic maturation of the oocyte seems to be crucial for events occurring from fertilization and onwards, including early cell-divisions of the pre-embryo, programming of the new genetic constitution of the embryo, implantation and, in fact, further development of the embryo/fetus. If the nuclear maturation and the cytoplasmatic maturation of the oocyte are not finely tuned events downstream to fertilization, implantation may be unsuccessful. Un-synchronization between these two events can probably explain the low success rate of IVM/IVF treatment in human and other mammals.

Physiological concentrations of FSH promote GVBD in cultured oocytes of the human (Byskov et al., 1997) and the monkey (Schramm and Bavister, 1995). It has been shown that FSH stimulates cumulus cells connected to the oocyte to synthesize substances, probably MAS, which positively promote maturation (Byskov et al., 1997; Yding Andersen et all 1999). A recent study indicated that by replacing these pre-embryos to pseudopregnant mice it was shown that the number of implantations was enhanced in the group with FSH present in the oocyte maturation medium compared to the control medium and almost similar to that of in vivo matured oocytes (Merriman et al., 1998). This indicates that FSH participates in both the nuclear and the cytoplasmatic maturation of oocytes, in vitro. The data presented in example 3 demonstrate that FSH induces resumption of meiosis via MAS.

EGF has been shown to enhance oocyte maturation in a number of species like the cow, the pig, the mouse and the rat, and one study showed that FSH up-regulated the expression of EGF receptors in rat granulosa cells (Maruo et al., 1993). Goud et al. (1998) found that EGF (2 ng/ml) enhanced the number of germinal vesicle oocytes reaching metaphase II (MII) after a 30 h culture and concluded that EGF improved the nuclear and the cytoplasmatic maturation of human oocytes in vitro.

Human oocytes, which are used for in vitro maturation, usually derive from women who have not received hormone stimulation or only a mild stimulation with exogenous gonadotropins. The oocytes are usually obtained from follicles before they have been exposed to the mid-cycle surge of gonadotropins. The oocytes are cultured in a basal medium, often supplemented with serum and gonadotropins (examples of gonadotropins are FSH and LH) for 24 to 48 hours in order for the nuclear maturation to occur and allow meiosis to resume. Thereafter, oocytes are fertilized either by conventional IVF or by ICSI and cultured for an additional two to five days in order for pre-embryo development to occur. When the pre-embryos have developed to a two-cell stage or further to the blastocyst stage they are replaced in the woman's uterus and she has the chance of conceiving and bearing a child.

The method of the present invention employs oocytes, which are retrieved from antral follicles of the ovaries before being exposed to the mid-cycle surge of gonadotropins and is therefore characterized as immature or not fully matured oocytes. Human oocytes as well as oocytes from other species will be recognized as having little or no cumulus expansion, a germinal vesicle and no polar bodies, and will readily be recognized as such by persons skilled in IVF-treatments.

In one embodiment of the present invention, the oocyte originates from a mammal, such as a pet, e.g. a cat, a dog, or a guinea pig; or a zoo animal e.g. a primate. In further preferred embodiments, the mammal is part of the industry, preferably a farm animal such as cattle, a horse, a pig, a mink, a goat, or a sheep. In the most preferred embodiment, the mammal is a human being.

For immature oocytes to mature into fertilizable oocytes competent of developing into viable conceptuses, two related but distinct processes seem to be important. The oocyte needs to undergo both a proper nuclear maturation and a proper cytoplasmatic maturation. Nuclear maturation encompasses the processes reactivating meiosis arrested at prophase I and stimulates the meiotic process to proceed to metaphase II, at which stage fertilization usually takes place. Oocytes arrested in prophase I exhibit a so-called germinal vesicle (GV-stage), in which the nuclear membrane and the nucleolus are visible through a microscope. Nuclear maturation becomes manifest when the oocyte undergo the so-called GV break down (i.e. GVBD). Cytoplasmatic maturation refers to the processes that prepare the oocyte for activation, formation of pronuclei and the developmental path undertaken until implantation has been accomplished. The competence to undergo both nuclear and cytoplasmatic maturation of GV-stage oocytes is usually acquired in a stepwise manner. For example, oocytes from mice first acquire competence to undergo fertilization and develop into two-cells, but further development of GV-stage oocytes is required before the oocytes achieve competence to develop from the two-cell stage into the blastocyst stage (Eppig and Schroeder, 1989). This has been further demonstrated in studies of mice oocytes, in which metaphase II oocytes from 18-day-old mice showed a reduced competence to develop into two-cells compared to metaphase II oocytes from 26-old-mice (82 versus 27%), demonstrating that even though both groups of oocytes had completed nuclear maturation by progressing to metaphase II, oocytes from the smaller follicles of the younger mice were deficient in cytoplasmatic factors essential for development of embryos beyond the 2-cell stage (Eppig et al., 1994). Thus, even though oocytes may be competent of completing nuclear maturation, they can still be lacking a sufficient cytoplasmatic maturation. These studies demonstrate that acquisition of competence of oocytes to complete nuclear maturation usually precedes the processes by which cytoplasmatic maturation is acquired.

This has further been illustrated by studies using immature monkey oocytes, where ooplasm (i.e. cytoplasmatic extracts from an oocyte) removed from a mature oocyte via micromanipulation is injected into immature oocytes. Those oocytes which received ooplasm from mature oocytes exhibited a sevenfold increase in pregnancy rate compared to oocytes receiving sham injection.

When the oocyte has undergone nuclear maturation and resumed meiosis it reaches a crossroad: If it is not fertilized in vivo or in vitro within a limited time interval of only around 12 h, it will deteriorate and no offspring will result (review: Wassarman and Albertini, 1994). The reason for this short fertilizable life span of the oocyte after nuclear maturation is not well understood. It has been suggested that the arrest of meiosis in the metaphase II may be regarded as a dynamic stage, in which the oocyte is ready and able to accomplish fertilisation. This dynamic stage is transient and can only be maintained for a limited period, after which the oocyte looses the ability to form viable offspring after fertilization. This activated stage is characterized by the presence of mature cortical granula and the presence of an intact spindle, which makes the oocyte especially vulnerable.

The use of gonadotropins for maturation of the oocytes in vitro also stimulates oocytes to resume meiosis. As pointed out above, oocytes may only be fertilised within a relative short time interval and therefore the oocytes may lack a sufficient cytoplasmatic maturation to acquire a pregnancy potential of a similar magnitude as to that of in vivo matured oocytes.

One problem resolved by the present invention is the low rate of implantation of in vitro matured, in vitro fertilized pre-embryos. By culturing one or more oocytes during in vitro maturation in the presence of at least one meiosis activating sterol (MAS) antagonist or agonist, a MAS being any sterol in the metabolic pathway between lanosterol and cholesterol, a MAS analogue, and/or an additive or additives capable of blocking or inhibiting an endogenous stimulation of the accumulation of at least one MAS, the nuclear maturation is stopped or blocked even in the presence of in supra-physiological concentrations of FSH and LH. The presence of gonadotropins, growth factors and other substances, which are present in the follicular compartment, will stimulate the cytoplasmatic maturation to proceed while nuclear maturation is retained.

It is preferred to culture the one or more oocytes during in vitro maturation in the presence of a MAS antagonist. However, due to the biological complexity it is presently anticipated that the addition of a MAS agonist will have the same effect due to the negative feed back.

It is therefore an aspect of the present invention to stop or block—selectively and reversibly—the nuclear maturation of oocytes in the presence of FSH and LH in order for the gonadotropin/growth factor induced cytoplasmatic maturation to proceed. After allowing cytoplasmatic maturation to occur for a time period, the substances blocking the nuclear maturation, that is the nuclear maturation inhibiting substance, is removed and the nuclear maturation is induced by gonadotropins, growth factors or MAS. This will allow oocytes to achieve a balanced and synchronized cytoplasmatic and nuclear maturation resembling that observed in vivo thereby increasing the pregnancy potential of resulting pre-embryos. By selectively and reversibly stopping or blocking the nuclear maturation from proceeding, the present invention takes advantages of the dual activities undertaken by FSH and LH, namely that they stimulate both the nuclear maturation and the cytoplasmic maturation of oocytes. Since competence to resume meiosis and complete nuclear maturation is achieved before full cytoplasmatic maturation has occurred, more competent oocytes are obtained as a result of the present invention, which allows gonadotropin stimulated cytoplasmatic maturation to occur.

This contrasts existing methods where the occurrence of the nuclear maturation defines the time of insemination with spermatozoa irrespective of whether sufficient cytoplasmatic maturation has taken place or not.

The term "nuclear maturation inhibiting substance" should be understood as a substance capable of inhibiting nuclear maturation without substantial effect on the cytoplasmatic maturation. A nuclear maturation inhibiting substance is a substance which is capable of inhibiting the formation of Polar Bodies or capable of inhibiting GVBD in mice oocytes isolated by puncturing individual follicles using a 25 gauge needle from ovaries recovered from immature female mice which had received 7.5 U/mouse of Gonadoplex 44–48 hours previously, and the oocytes grown in α-MEM with EBSS, 200 µM dbc-AMP or 4 mM hypoxanthine, 3 mg/ml BSA, 0,23 mM pyrovate, 2 mM glutamine, 100 IU/ml penicillin and 100 mg/ml steptomycin, followed by washing 3 times in the medium and culture for 22–24 hours in 100% humidified atmosphere of 5% $CO_2$ with 95% air at 37° C. Ketoconazole is an example of such substance, as shown in examples 1 and 2.

Thus, in one aspect of the invention the nuclear maturation inhibiting substance can be defined as a substance which is capable of inhibiting the formation of Polar Bodies, capable of inhibiting GVBD, or capable of decreasing the PB/GVBD ratio without having substantial effect on the cumulus expansion in the oocytes. 22-hydroxycholesterol is an example of such substance, as shown in example 3.

The term "cytoplasmatic maturation" is well known in the art. However, no exact definition of individual components and their role in the process is established. The term is usually defined as the extragenomic changes that prepare the egg for activation, pronuclear formation, and early embryogenesis. In one aspect of the present invention cumulus expansion is one measurable aspect of cytoplasmatic maturiation. When observing oocytes in the microscope the cumulus expansion can be graded as 0: No expansion, compact cumulus layer surrounding the oocyte;

+: A slight cumulus expansion, the most peripheral cumulus cell looks a little fluffy;

++: good expansion of cumulus cell without a spherical cloud like expansion;

+++: full cumulus expansion with a fluffy cloud like expansion with extended distance between the somatic cells.

In connection with the present invention it has therefore surprisingly been shown that nuclear maturation can be stopped or blocked in presence of FSH (75 IU/L), when oocytes are cultured in the presence of substances which interfere and reduce the synthesis of Meiosis Acitivating Sterols (MAS), which are known to induce nuclear maturation of oocytes in mice and man (Byskov et al., 1995, Grøndahl et al., 1999).

It is therefore an aspect of the present invention to grow oocytes in vitro in presence of substances, which inhibit or reduce the synthesis of MAS (i.e. ketoconazole) for a period of 2 to 96 hours in order for the cytoplasmatic maturation to occur within the oocytes, after which the inhibiting substance is removed and a gonadotropin, growth factor or MAS induced nuclear maturation is obtained, which will be followed by fertilization after the oocyte has reached the metaphase II stage either with ICSI or by a normal conventional fertilization in vitro. The resulting embryos will be transplanted to the uterus of the woman as for conventional IVF-procedures. This will allow a synchronization of the nuclear and cytoplasmatic maturation of oocytes before embarking on further development such as fertilization, embryo development and possibly implantation.

It is a preferred aspect that the cytoplasmatic maturation is promoted and nuclear maturation retained within a period of 2 to 96 hours.

It is preferred that the concentration of ketoconazole is between 1 and 100 μM.

In the preferred embodiment, the immature oocytes are matured in commercially available chemically defined medium as used for the culture of cells supplemented with an agent blocking the nuclear maturation as described above, gonadotropins, growth factors (an example of a growth factor is EGF), plus varying amounts of serum deriving from the woman herself or follicular fluid which surrounds the oocyte in its natural environment. The follicular fluid is characterised by having concentrations of steroids (e.g. oestradiol, androgens and progestins) which are several orders of magnitude higher that those in circulation and in order to simulate the natural environment addition of exogenous hormones to the culture medium is used in yet another embodiment of the invention.

Following cytoplasmatic maturation in a preferred embodiment of the present method, the nuclear maturation of the oocytes is performed in a culture medium, which is a commercially available chemically defined medium as used for the culture of cells supplemented with gonadotropins and/or growth factors and/or MAS plus varying amounts of serum deriving from the woman herself or follicular fluid which surrounds the oocyte in its natural environment. Addition of exogenous steroids as described above is used in yet another embodiment of the nuclear maturation process.

These steps are followed by the regular steps for IVF, known to the person skilled in the art.

REFERENCES

Barnes F L, Kausche A K, Tiglias J et al. (1996) Production of embryos from in vitro matured primary oocytes. Fertil. Steril., 65, 1151–56.

Byskov A G, Yding Andersen C, Nordholm L et al. (1995) Chemical structure of novel meiosis activating steroids crucial to reproduction. Nature, 374, 559–62.

Byksov A G, Yding Andersen C, Hossaini A et al. (1997) Cumulus cells of oocyte-cumulus complexes secrete a meiosis-activating substance when stimulated with FSH. Mol. Reprod. Dev. 46, 296–305.

Cha K Y, Koo J J, Ko J J et al. (1991) Pregnancy after in vitro fertilisation of human follicular oocytes collected from nonstimulated cycles, their culture in vitro and their transfer in a donor oocyte program. Fertil. Steril., 55, 109–13.

Cha K Y, Chian R C (1998) Maturation in vitro of immature human oocytes for clinical use. Hum. Reprod. Update, 4, 103–20.

Eppig J J, Schroeder A C (1989) Capacity of mouse oocytes from preantral follicles to undergo embryogenesis and development to live young after growth, maturation and fertilization in vitro. Biol. Reprod., 41, 268–76.

Eppig J J, Schultz R M, O'Brien M et al. (1994) Relationship between the developmental programs controlling nuclear and cytoplasmatic maturation of mouse oocytes. Devel. Biol., 164, 1–9.

Goud P T, Goud A P, Qian C et al. (1998) In-vitro maturation of human germinal vesicle stage oocytes: role of cumulus cells and epidermal growth factor in the culture medium. Hum. Reprod. 13, 1638–1644.

Maruo T, Ladines-Llave C A, Samoto T et al. (1993) Expression of epidermal growth factor and its receptor in the human ovary during follicular growth and regression. Endocrinology, 132, 924–931.

Meriman J A, Whittingham D G, Carroll J (1998) The effect of follicle stimulating hormone and epidermal growth factor on the development capacity of in-vitro matured mouse oocytes. Hum. Reprod., 13, 690–95.

Mikkelsen A L, Smith S D, Lindenberg S (1999) In-vitro maturation of human oocytes from regularly menstruating women may be successful without follicle stimulation hormone priming. Hum. Reprod., 14, 1847–51.

Russell J B, Knezevich K M, Fabian K et al. (1997) Unstimulated immature oocyte retrieval: early versus midfollicular endometrial priming. Fertil. Steril., 67, 616–20.

Schramm R D, Bavister B D (1995) Effects of granulosa cells and gonadotropins on meiotic and developmental competence of oocytes in vitro in non-stimulated rhesus monkeys. Hum. Reprod., 10, 887–895.

Trounson A, Wood C, Kaunsche A (1994) In vitro maturation and fertilization and developmental competence of oocytes recovered from untreated polycystic ovarian patients. Fertil. Steril., 62, 353–62.

Wassarman P M, Albertini D F (1994) The mammalian ovum. In Knobil E and Neill J D (eds), The Physiology of Reproduction, $2^{nd}$ edition, Raven Press, New York, pp. 79–122.

Yding Andersen, C., Westergaard, L. et Byskov, A. G (1999) Follicle-stimulating hormone and epidermal growth factor augment the implantation rate of human pre-embryos; 11th World Congress on In vitro fertilization & human reproductive genetics.

EXAMPLES

Example 1

Effect of Ketoconazole on FSH Induced Resumption of Meiosis of Mouse Oocytes Cultured in Vitro.

Immature female mice (B6D2-F1 strain C57B1/2J) were kept under controlled light and temperature conditions with free access to food and water. Ovarian stimulation was performed when the mice weighed 10–16 grams and consisted of an intra-peritoneal injection of Gonadoplex (Leo, Copenhagen, Denmark) containing 7.5 U/mouse. The animals were killed by cervical dislocation 44–48 h later. The media used for the culture of oocytes consisted of α-Minimum Essential Medium (α-MEM), with Earles Balanced Salt Solution (EBSS), 200 μM dibuturyl-cyclic-adenosine-mono-phosphate (dbc-AMP), 3 mg/ml Bovine Serum Albumin, 0,23 mM pyruvate, 2 mM glutamine, 100 IU/ml penicillin and 100 mg/ml streptomycin (i.e. control medium). The ovaries were recovered and oocytes isolated from the ovaries by puncturing individual follicles using a 25 gauge needle. The oocytes were washed 3 times in control medium before the start of each experiment. Cumulus enclosed oocytes were cultured separately in 4-well dishes (Nuncleon, Roskilde, Denmark), 0.4 ml medium in each well containing control medium or medium supplemented with ketoconazole in a 100% humidified atmosphere of 5% $CO_2$ with 95% air at 37° C. The culture period was 22–24 h. By the end of the culture period, germinal vesicle breakdown (GVBD) was scored by examining the oocyte in an inverted microscope. The percentage of oocytes with GVBD per total number of oocytes (% GVBD) was calculated.

To the control medium FSH (Metrodin H P, Serono Nordic, Denmark) 75 IU/L was added. To the medium containing FSH 75 IU/L increasing concentrations of ketoconazole was added (i.e. 5, 10 and 20 μM) and all five media were subjected to culture together with mouse oocytes.

TABLE 1

|  | no. oocytes | % GVBD | % PB (PB/GVBD) |
|---|---|---|---|
| Control medium | 193 | 5 | 11 |
| FSH 75 IU/L | 510 | 31 | 66 |
| Ketoconazole 5 μM | 102 | 7 | 57 |
| 10 μM | 175 | 7 | 8 |
| 20 μM | 39 | 3 | 0 |

The percent of GVBD achieved by FSH 75 IU/L is significantly higher than in any of the other groups ($P<0.05$). The percentage of GVBD between groups with ketoconazole and the control are all similar. The percentage of Polar Body (PB) formation is significantly higher in the group receiving FSH alone compared to the control group and the group receiving ketoconazole in 10 and 20 μM.

The results presented in table 1 demonstrate that ketoconazole is able to prevent oocytes resuming meiosis and keep resumption of meiosis at a level similar to that of the control. Not only is ketoconazole able to prevent resumption of meiosis but at concentrations of 10 and 20 μM, the formation of polar bodies is also compromised, showing that oocytes at which the germinal vesicle disappears do not reach metaphase II.

It has been shown that FSH induces cumulus cells of intact cumulus oocyte complexes to produce MAS (WO 00/52142). Since ketoconazole inhibits the enzymes in the biosynthetic pathway to cholesterol, the present results demonstrate that a stopping or blocking the stimulation of an endogenous accumulation of MAS, will prevent an FSH induced nuclear maturation without affecting other FSH induced processes within the cumulus complex and the oocyte.

Ketaconazol is the generic name of a compound, which is used for medical treatment in order to combat infections with e.g. fungi, the active principle being an inhibition of cholesterol biosynthesis in the fungi. However, the substance does not seem to have any serious side effects in connection with use in humans.

Example 2

Effect of Ketoconazole on FSH Induced Resumption of Meiosis of Hypoxanthine Arrest Mouse Oocytes Cultured in Vitro.

Oocytes were obtained from immature mice (Kunming white mouse) weighing 14–16 g that were kept under controlled light and temperature conditions with free access to water. The mice received an intra peritoneal injection of 0.1 ml pregnant mare's serum gonadotrophin (PMSG, Sigma, New York, U.S.A) containing 10 IU PMSG. Forty-six hours later, the animals were killed by cervical dislocation. The ovaries were dissected out and placed in M199 culture medium (GIBCO, U.S.A) containing 4 mM hypoxanthine, 3 mg/ml bovine serum albumin, 0.23 mM pyruvate, 2 mM glutamine (all Sigma, U.S.A) and 100 IU/ml penicillin, 100 ug/ml Streptomycin. This medium was termed "HX-medium". A media similar to the above but without HX are termed "maturation-medium". Oocytes were isolated in HX-medium under a stereo microscope by manual rupture of follicles using a pair of 5.5-gauge needles. Spherical oocytes with intact cumulus cells connection and displaying germinal vesicle were categorized as cumulus-enclosed oocytes (CEO). Oocytes were rinsed 3 times in fresh HX-medium. Prior to each experimental set-up, all oocytes from 10–15 mice were pooled. Only oocytes with a germinal vesicle present were used and distributed in separate wells of a 4-well dish (Nuncoln, Denmark) containing 1 ml of HX-medium. Each well contained 20–30 oocytes and was cultured at 37° C. in 1000% humidity in air with 5% $CO_2$. Each experiment was repeated at least 4 times. At the end of the culture period (i.e 24 h), oocytes with GV or GVBD, or polar body (PB) were counted using an inverted microscope with differential interference contrast equipment (Leica, German). The percentage of oocytes with GVBD per total number of oocytes (% GVBD) and the percentage of oocytes with PB formation per total number of oocytes (% PB) were calculated.

To the control medium FSH (Sigma, New York, USA) 50 IU/L was added. To the medium containing FSH 50 IU/L increasing concentrations of ketoconazole is added (i.e. 0.1, 1, 10, 100 and 1000 μM) and all media were subjected to culture together with mouse oocytes.

TABLE 2

|  |  | no. oocytes | % GVBD | % PB (PB/GVBD) |
|---|---|---|---|---|
| Control medium |  | 90 | 28 | 19 |
| FSH 50 IU/L |  | 90 | 59 | 35 |
| Ketoconazole | 0.1 μM | 90 | 58 | 33 |
|  | 1 μM | 90 | 48* | 30 |
|  | 10 μM | 90 | 35* | 25 |
|  | 100 μM | 90 | 20* | 19* |
|  | 1000 μM | 90 | 21* | 17* |

*Indicate significant differences compared to the group cultured with FSH 50 IU/L alone. Data are pooled from three individul experiments.

The results presented in table 1 demonstrate that ketoconazole prevents oocytes from resuming meiosis and keep nuclear maturation at a level similar to that of the control. As indicated in example 1, a dose-dependant inhibition of PB formation is seen, showing that oocytes at which the germinal vesicle disappears less frequent reach metaphase II.

It has been shown that FSH induces cumulus cells of intact cumulus oocyte complexes to produce MAS (WO 00/52142). Since ketoconazole inhibits the enzymes in the biosynthetic pathway to cholesterol, the present results demonstrate that a stopping or blocking of the stimulation of an endogenous accumulation of MAS, will prevent an FSH induced nuclear maturation without affecting other FSH induced processes within the cumulus complex and the oocyte.

Example 3

Effect of 22-Hydroxycholesterol on FSH Induced Resumption of Meiosis of Hypoxanthine Arrest Mouse Oocytes Cultured in Vitro.

Immature female mice (B6D2-F1 strain C57B1/2J) were kept under controlled light and temperature conditions with free access to food and water. Ovarian stimulation was performed when the mice weighed 10–16 grams and consisted of an intra-peritoneal injection of Gonadoplex (Leo, Copenhagen, Denmark) containing 7.5 U/mouse. The animals were killed by cervical dislocation 44–48 h later. The media used for the culture of oocytes consisted of α-Minimum Essential Medium (α-MEM), with Earles Balanced Salt Solution (EBSS), containing 4 mM hypoxanthine, 3 mg/ml bovine serum albumin, 0.23 mM pyruvate, 2 mM glutamine (all Sigma, U.S.A) and 100 IU/ml penicillin, 100 ug/ml Streptomycin. This medium was termed "HX-medium". A media similar to the above but without HX are termed "maturation-medium". Oocytes were isolated in HX-medium under a stereo microscope by manual rupture of follicles using a pair of 5.5-gauge needles. Spherical oocytes with intact cumulus cells connection and displaying germinal vesicle were categorized as cumulus-enclosed oocytes (CEO). Oocytes were rinsed 3 times in fresh HX-medium. Prior to each experimental set-up, all oocytes from 10–15 mice were pooled. Only oocytes with a germinal vesicle present were used and distributed in separate wells of a 4-well dish (Nuncoln, Denmark) containing 1 ml of HX-medium. Each well contained 20–30 oocytes and was cultured at 37° C. in 100% humidity in air with 5% $CO_2$. Each experiment was repeated at least 4 times. At the end of the culture period (i.e 24 h), oocytes with GV or GVBD, or polar body (PB) were counted using an inverted microscope with differential interference contrast equipment (Leica, German). The percentage of oocytes with GVBD per total number of oocytes (% GVBD) and the percentage of oocytes with PB formation per total number of oocytes (% PB) were calculated.

To the control medium FSH (Puregon, Organon, Oss, The Netherlands) 75 IU/L was added. To the medium containing FSH 75 IU/L, 22-hydroxycholesterol in the designated concentrations was added and all media were subjected to culture together with mouse oocytes.

TABLE 3

Experiments without the presence of fetal calf serum in the medium

| | no. oocytes | % GVBD | % PB (PB/GVBD) | Cumulus expansion |
| --- | --- | --- | --- | --- |
| Control medium | 100 | 21 | 29 | (+) |
| 22-OH-cholesterole 3 µg/ml | 108 | 26 | ND | ND |
| FSH 75 IU/L | 60 | 55 | 76 | +(+) |
| FSH (75 IU/L) + 22-OH-cholesterole 1 µg/ml | 39 | 62 | 25* | ND |
| FSH (75 IU/L) + 22-OH-cholesterole 5 µg/ml | 43 | 72 | 26* | ND |
| FSH (75 IU/L) + 22-OH-cholesterole 10 µg/ml | 63 | 31* | 11* | +(+) |
| FSH (75 IU/L) + 22-OH-cholesterole 25 µg/ml | 84 | 17* | 0* | ND |

*Indicate significant differences compared to the group cultured with FSH 75 IU/L alone.

TABLE 4

Experiments with the presence of fetal calf serum in the medium.

| | no. oocytes | % GVBD | % PB (PB/GVBD) | Cumulus expansion |
| --- | --- | --- | --- | --- |
| Control medium | 148 | 29 | 37 | + |
| FSH 75 IU/L | 134 | 54 | 56 | +++ |
| FSH (75 IU/L) + 22-OH-cholesterole 1 µg/ml | 34 | 41 | 29 | +++ |
| 10 µg/ml | 57 | 39* | 14* | ++(+) |
| 25 µg/ml | 153 | 19* | 28* | ++(+) |

*Indicate significant differences compared to the group cultured with FSH 75 IU/L alone.

Graduation of cumulus expansion: 0: No expansion, compact cumulus layer surrounding the oocyte; +: A slight cumulus expansion, the most peripheral cumulus cell looks a little fluffy; ++: good expansion of cumulus cell without a spherical cloud like expansion; +++: full cumulus expansion with a fluffy cloud like expansion with extended distance between the somatic cells.

The results presented in table 3 and 4 demonstrate that 22-hydroxycholesterol prevents oocytes from resuming meiosis in the presence of FSH and keep nuclear maturation at a level similar to that of the control and that of 22-hydroxycholesterol alone in a concentration of 3 µg/ml. In the presence of 5% fetal calf serum, a higher concentration of 22-hydroxycholesterol is required to obtain a similar inhibition as without serum. This probably reflects that 22-hydroxycholesterol is bound to proteins in the fetal calf serum, thereby decreasing the concentration available for biological action. Cumulus expansion is induced by FSH, but the presence of serum is required for full expansion. Cumulus expansion can be considered as one aspect of cytoplasmatic maturiation. The results of tables 3 and 4 demonstrate that cumulus expansion occurs to similar degree in the presence of 22-hydroxycholesterol and FSH, as with FSH alone, demonstrating that it is possible to separate nuclear and cytoplasmatic maturation, and that the FSH receptor mediated processes that govern cytoplasmatic maturation is not affected by the blocking of the nuclear maturation by 22-hydroxycholesterol.

Thus, in combination with the information given in WO 98/28323 in which it is shown that 22-hydroxycholesterol can prevent a FF-MAS induced resumption of meiosis in cultured mouse oocytes, the present results demonstrate for the first time that FSH induces resumption of meiosis via MAS, and that this effect can be blocked by the addition of 22-hydroxycholesterol.

The invention claimed is:

1. A method for in vitro maturation of oocytes, said method comprising the steps of: (a) culturing one or more germinal vesicle (GV) oocytes in a culture medium for a time period sufficient for cytoplasmatic maturation to occur, wherein the culture medium comprises a nuclear maturation inhibiting substance and one or more gonadotropins and/or one or more growth factors; (b) washing the GV oocytes of step (a) to remove the nuclear maturation inhibiting substance; (c) culturing the washed oocytes of step (b) in a culture medium comprising one or more gonadotropins and/or one or more growth factors and/or meiosis activating sterols (MAS) for a time period sufficient for nuclear maturation to occur.

2. A method according to claim 1, wherein the GV oocytes are cultured with the nuclear maturation inhibiting substance for 2–96 hours.

3. A method according to claim 1, wherein the nuclear maturation inhibiting substance is a compound capable of selective inhibition of meiosis activating sterol (MAS) synthesis or is a MAS antagonist.

4. A method according to claim 1, wherein the one or more gonadotropins and/or one or more growth factors are a combination of epidermal growth factor (EGF) and follicle stimulating hormone (FSH) and/or luteinizing hormone (LH).

5. The method according to claim 1, wherein the nuclear maturation inhibiting substance is a 4,4-dimethyl-5.alpha.-cholesta-8,14,24-triene-3-B-ol (FF-MAS) synthesis inhibitor.

6. The method according to claim 5, wherein the FF-MAS synthesis inhibitor is a cytochrome P450 lanosterol 14.alpha.-demethylase (P45014DM) inhibitor.

7. The method according to claim 5, wherein the FF-MAS synthesis inhibitor is ketoconazole.

8. The method according to claim 5, wherein the FF-MAS synthesis inhibitor is 22-hydroxycholesterol.

9. The method according to claim 5, wherein the one or more gonadotropins and/or one or more growth factors are a combination of epidermal growth factor (EGF) and follicle stimulating hormone (FSH) and/or luteinizing hormone (LH).

10. The method according to claim 6, wherein the one or more gonadotropins and/or one or more growth factors are a combination of epidermal growth factor (EGF) and follicle stimulating hormone (FSH) and/or luteinizing hormone (LH).

11. The method according to claim 7, wherein the one or more gonadotropins and/or one or more growth factors are a combination of epidermal growth factor (EGF) and follicle stimulating hormone (FSH) and/or luteinizing hormone (LH).

12. The method according to claim 8, wherein the one or more gonadotropins and/or one or more growth factors are a combination of epidermal growth factor (EGF) and follicle stimulating hormone (ESH) and/or luteinizing hormone (LH).

* * * * *